United States Patent [19]
Pratt et al.

[11] Patent Number: 4,655,739
[45] Date of Patent: Apr. 7, 1987

[54] GAUZE FOLDING MACHINE

[75] Inventors: Robert H. Pratt, 7912 N. Beach Dr., Fox Point, Wis. 53217; Glen R. Blok, Milwaukee, Wis.

[73] Assignee: Robert H. Pratt, Fox Point, Wis.

[21] Appl. No.: 599,524

[22] Filed: Apr. 12, 1984

[51] Int. Cl.⁴ .................... B31B 23/14; B31B 23/26; B42C 1/04
[52] U.S. Cl. ................................. 493/357; 493/424; 493/427; 493/428; 493/431; 493/432; 493/356; 493/406; 270/42; 270/50
[58] Field of Search ............ 493/424, 425, 426, 427, 493/428, 431, 432, 937, 413, 357, 356, 406; 270/42, 43, 47, 49, 51; 414/107

[56] References Cited
U.S. PATENT DOCUMENTS

| 1,173,950 | 2/1916 | Seymour | 270/47 |
| 2,328,814 | 9/1943 | Laukhuff | 493/424 |
| 2,335,431 | 11/1943 | Meyer | 270/43 |

FOREIGN PATENT DOCUMENTS 2714915 10/1978 Fed. Rep. of Germany ........ 270/47

Primary Examiner—Robert L. Spruill
Assistant Examiner—David B. Jones
Attorney, Agent, or Firm—Fuller, Puerner & Hohenfeldt

[57] ABSTRACT

Apparatus for continuously manufacturing surgical sponges from a web of gauze is disclosed. The apparatus cuts the web into discrete pieces, and thereafter folds, irons, stacks and counts the pads as an integrated and automated operation at a high rate of speed.

18 Claims, 23 Drawing Figures

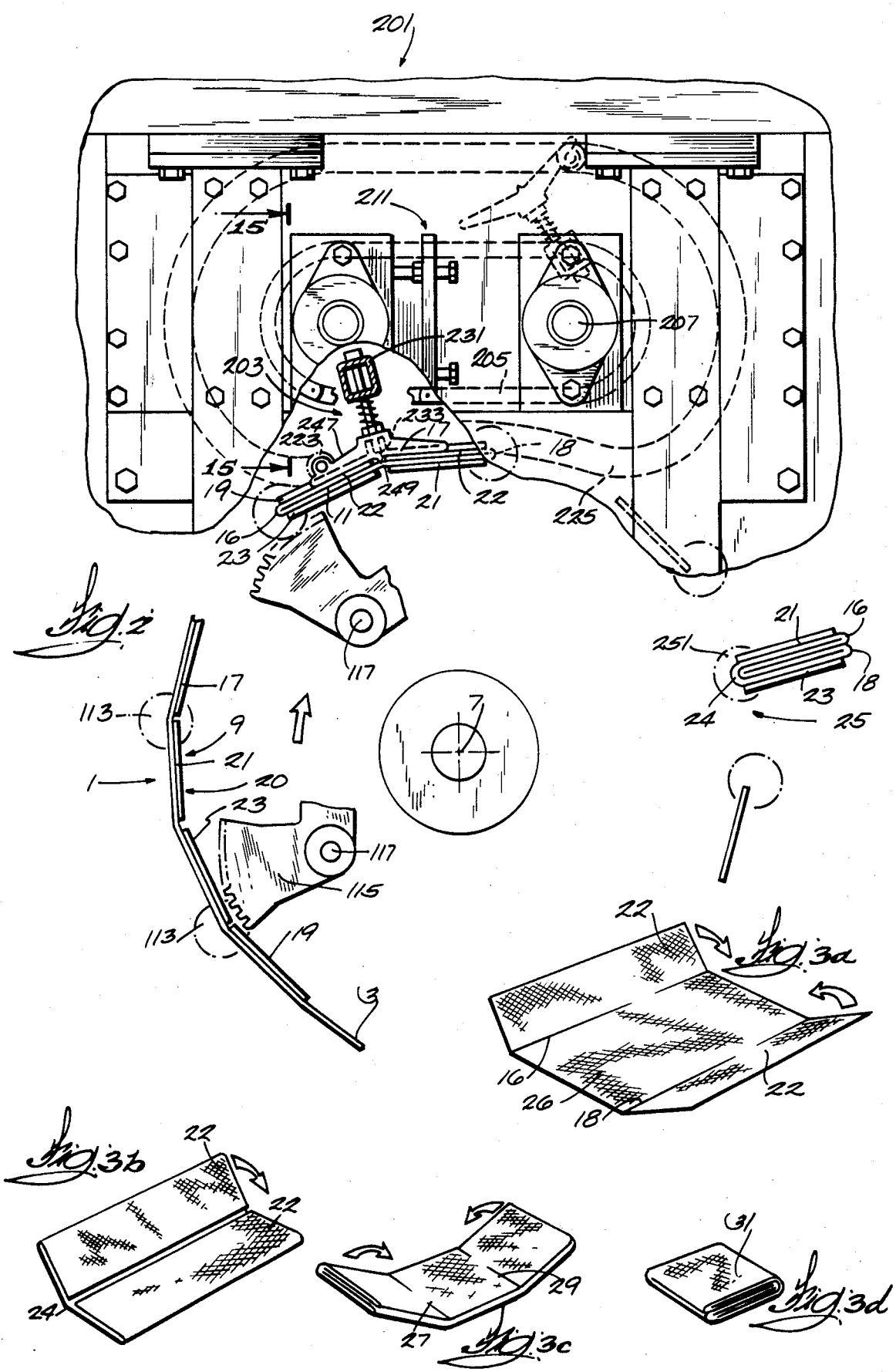

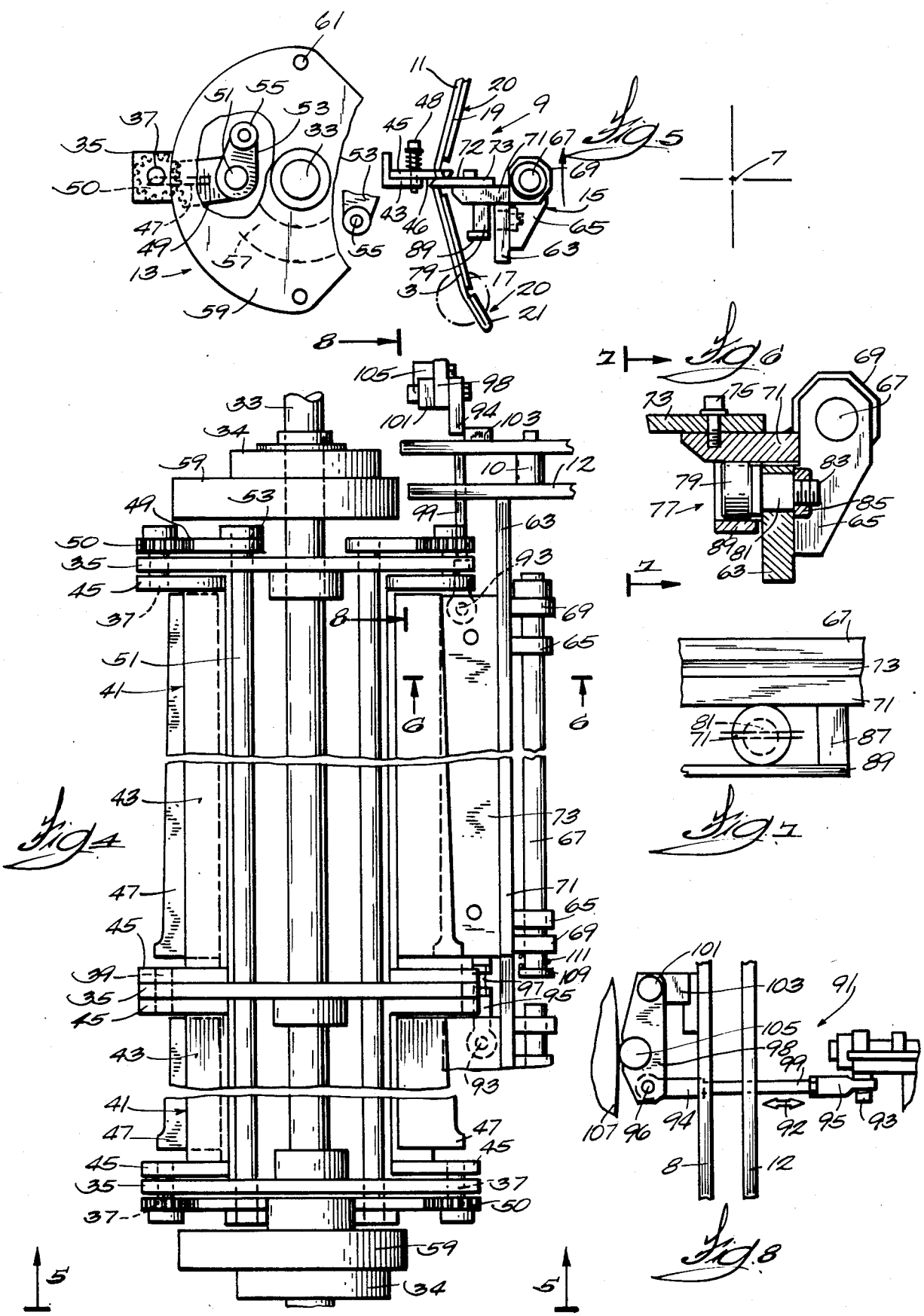

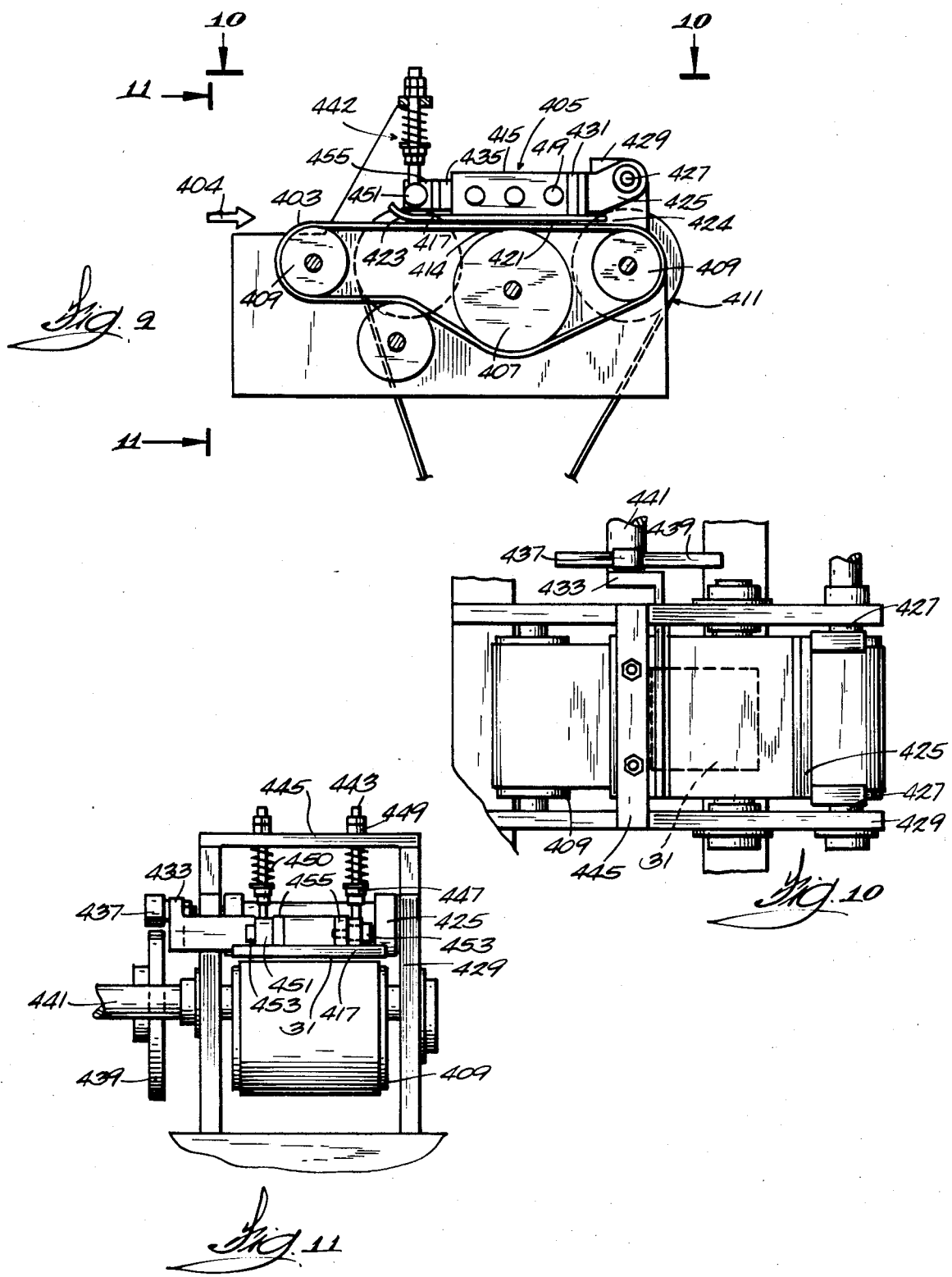

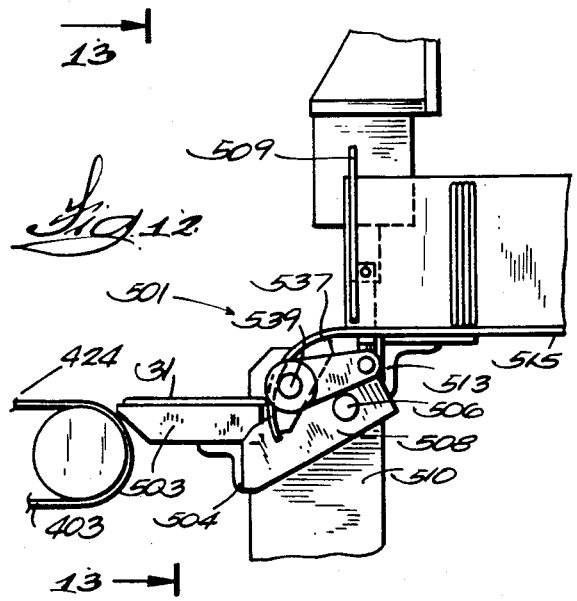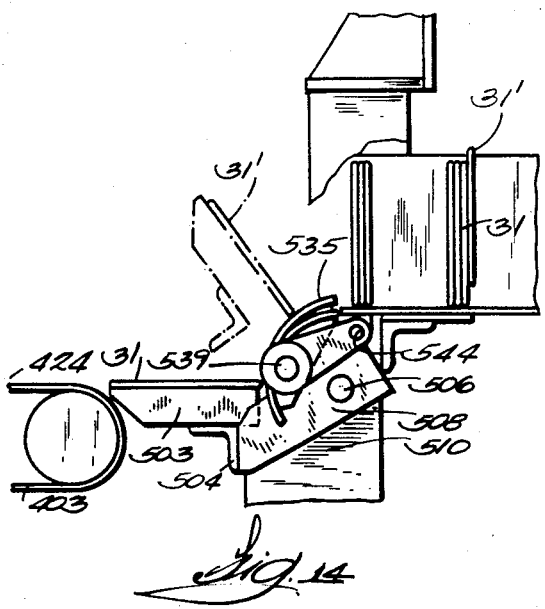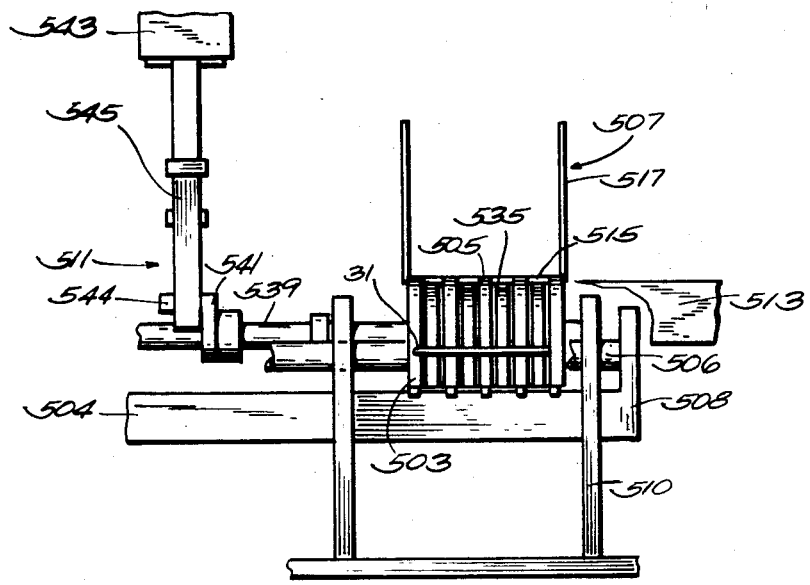

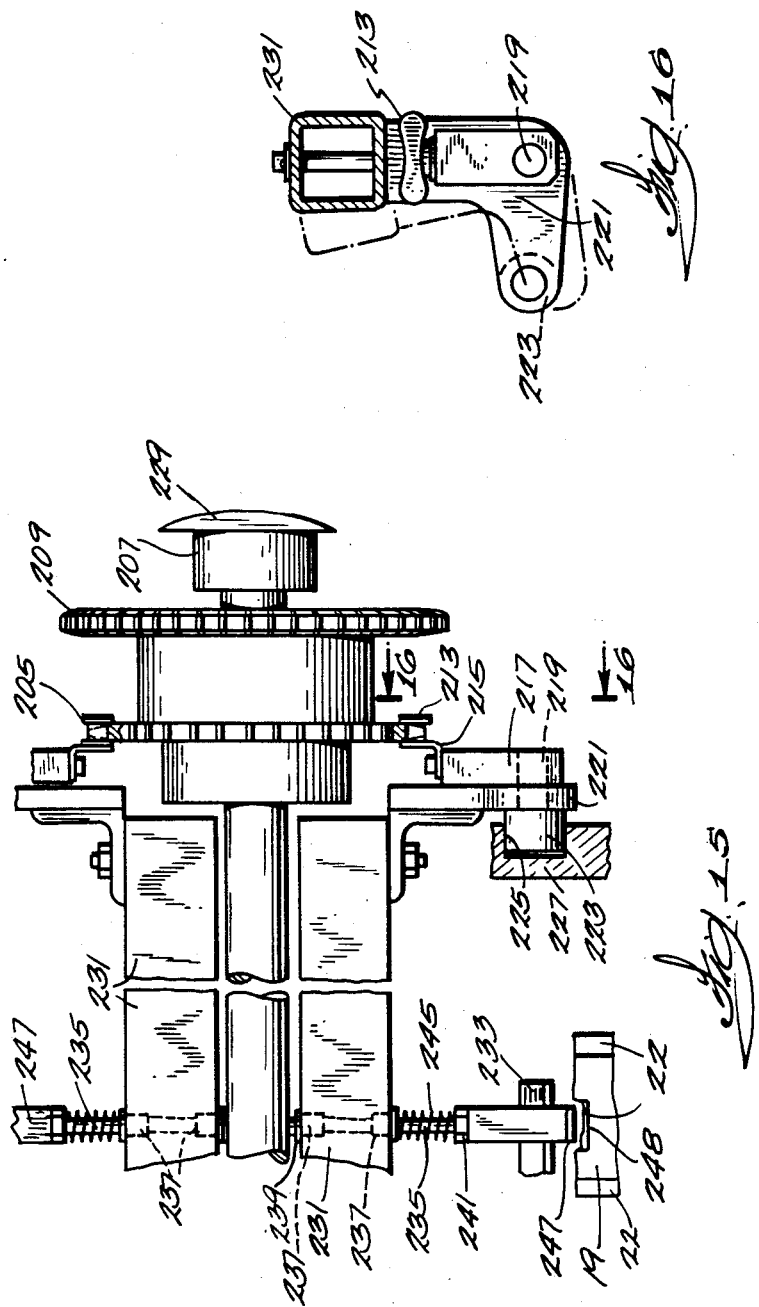

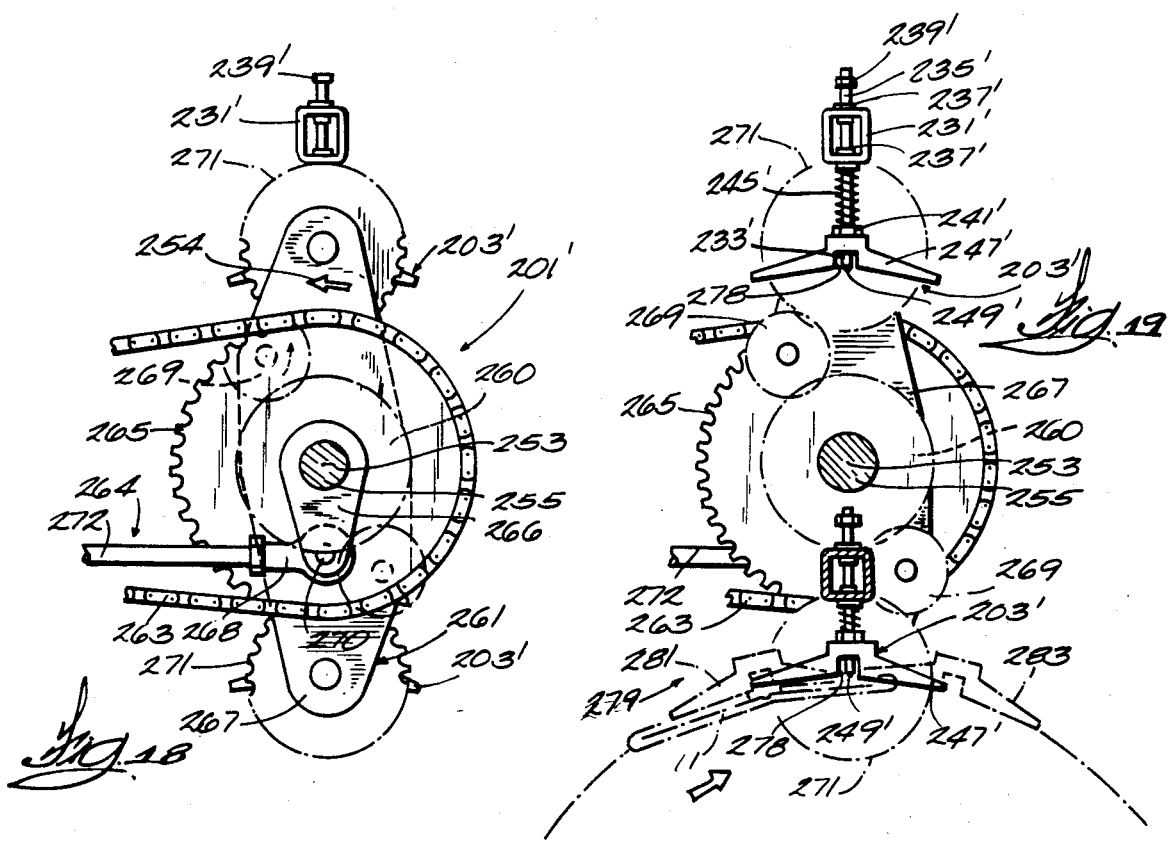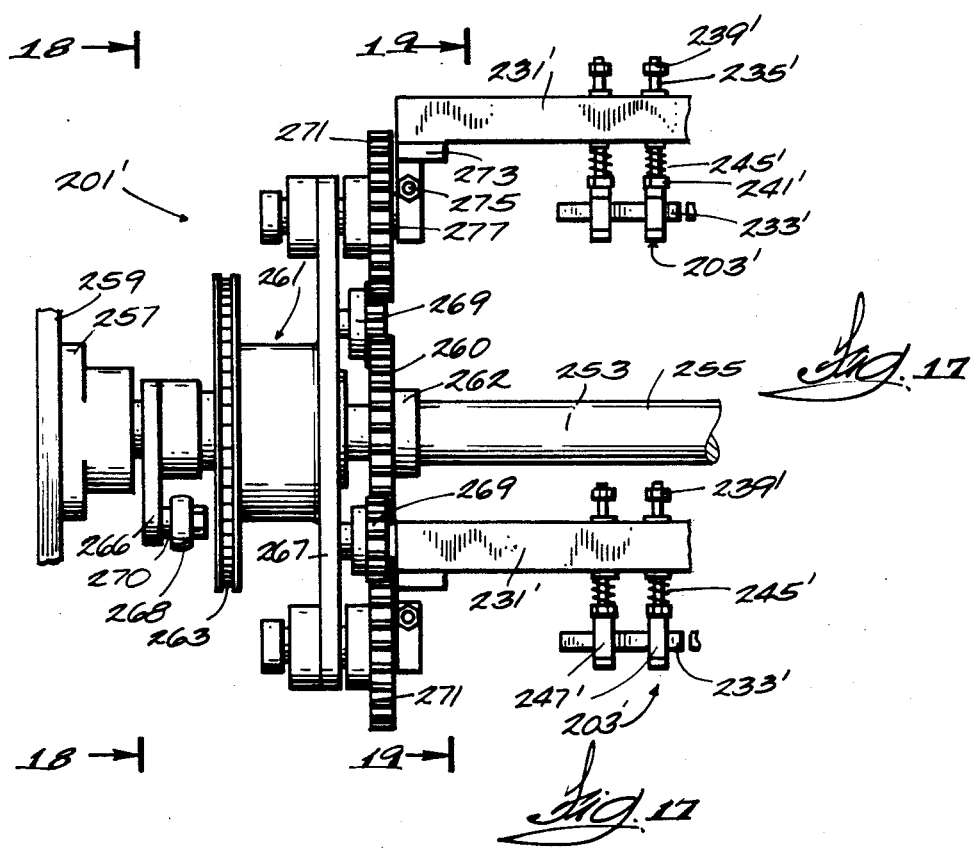

GAUZE FOLDING MACHINE

BACKGROUND OF THE INVENTION

1. Field of the Invention

This invention pertains to apparatus for manufacturing folded pads from material cut from a continuous web, and more particularly to apparatus for cutting pieces of textile-like material from a continuous web and thereafter folding the pieces into folded pads and ironing, stacking, and counting the pads.

2. Description of the Prior Art

U.S. Pat. No. 2,328,814 illustrates exemplary apparatus for cutting a continuous web of textile material into individual pieces and then folding the pieces along three fold lines. The primary application of the machinery embodied in the U.S. Pat. No. 2,328,814 patent is to cut and fold gauze into pads useful as surgical sponges. However, the apparatus may also be utilized to cut and fold paper and other materials for diverse purposes.

Subsequent to cutting and folding, the gauze pads are typically stacked and counted. U.S. Pat. No. 3,054,517 teaches a preferred machine for stacking and counting the folded pads after they are cut and folded on a machine similar to that described in U.S. Pat. No. 2,328,814. The pads are transferred by means of fingers from the folding machine to discharge chutes wherein the pads are stacked vertically on their edges. Electrical circuitry counts the number of pads entering the chute. After a predetermined number has entered the chute, a suitable mechanism displaces a pad horizontally or vertically from the other pads, thus giving a visual signal that a complement of the required number of pads has entered the chute.

The manufacture of folded gauze pads preferably includes the step of ironing them. Ironing assures that the pads retain their flat, folded configurations. To accomplish that purpose, apparatus such as shown in U.S. Pat. No. 3,193,953 has been successfully employed. Each folded pad is carried over a heated concave surface by a rotating ironer covered with a flexible covering material, such as canvas.

The previously described machines have enjoyed considerable commercial success. Nevertheless, all are somewhat deficient in light of modern production requirements. For example, the cutting and folding machine illustrated in U.S. Pat. No. 2,328,814 employs a large number of reciprocating, oscillating and cam driven parts. Operational speeds that meet contemporary demands result in high acceleration forces and stresses on the reciprocating and oscillating members. Excessive wear on cams and vibrations may also be a problem. Consequently, there is a need for a cutting and folding machine that is suited to continuous high speed operation.

It is presently considered desirable to iron the folded gauze pads prior to stacking and counting them. The ironing device disclosed in U.S. Pat. No. 3,193,953 is difficult to integrate into the overall manufacturing system. Additionally, the previous ironer is not entirely reliable, because the leading edge of a pad occasionally protrudes ahead of the rotary iron. In those instances, the pad is not ironed uniformly, and an unironed bulge remains. It is therefore desirable to improve the pad ironing apparatus.

The stacking and counting device of the 3,054,517 patent, although generally satisfactory, nevertheless possesses some shortcomings. For example, horizontal displacement of a selected pad presents a problem; as the vertically stacked pads are shoved down the discharge chute, the side walls of the chute tend to push the displaced pad back into line with the other pads. As a result, the displaced pad is sometimes difficult to detect. Thus, a need exists for a stacking and counting device that reliably indicates a complement of finished pads.

SUMMARY OF THE INVENTION

The present invention provides an integrated assembly of apparatus for manufacturing folded pads of textile or other material which are particularly suitable for surgical sponges or other folded product. The apparatus operates continuously at high speeds with a minimum of acceleration-induced stresses, vibrations and shock. This is accomplished by employing a maximum number of rotating components and by employing reciprocating and oscillating parts only when unavoidable. The manufacturing system includes a rotary drum-like apparatus which unwinds the material from a supply roll as a continuous web. The drum surface may be coated with a fabric to which the web material tends to cling. At a cutting station located at a fixed position relative to the drum, the web is cut into discrete pieces of material. The cutting mechanism comprises cooperating inner and outer rotating knife means. Each knife means carries a knife which engages a corresponding knife on the other knife means to cut the web. Both knife means are primarily rotational in nature so that they may be operated in conjunction with the drum at relatively high speeds. Subsequent to being cut, notched pivotable paddles carried by the drum fold the pieces along two initial fold lines.

The apparatus of the present invention includes presser feet which are mounted to an overhead mechanism for movement in synchronization with the drum. The presser feet engage the folded piece on the drum between the notches of the pivotable paddles while the paddles open. Thereafter, as the drum continues to rotate, a second set of notched paddles pivot to fold the piece along a third fold line parallel to the previous two fold lines. Finally, the folded piece is removed from the drum at a transfer station, which is located approximately diammetrically opposite the cutting station. At the transfer station, the thrice-folded piece is folded along two additional fold lines perpendicular to the original three fold lines to create a completely folded part.

In keeping with the invention, the folded pad is transferred from the transfer station to an ironer station. The ironer station comprises a horizontal belt which transports the pad between a pressure roller and a heated spring-loaded shoe. Cam means raise and lower the show to allow timed entry of the pad between the roller of the shoe. The springs apply correct ironing force.

The folded pad manufacturing assembly is also concerned with apparatus for manipulating the ironed pads to facilitate packaging them. For that purpose, the ironer belt conveys the ironed pads to a stacking and counting station at which the pads are stacked on their edges in a discharge chute. Electronic circuitry counts the number of pads entering the chute. The circuitry is designed so that it operates a mechanism to raise predetermined pads in the chute relative to the other pads. Thus, a convenient visual indication of a complement containing the desired number of pads is provided.

DESCRIPTION OF THE DRAWINGS

The advantages of the present invention will be more readily apparent upon reading the following detailed description and upon referring to the accompanying drawings, in which:

FIG. 2 is a partially schematic end view of the rotating drum and a presser foot mechanism;

FIG. 3 (a) is a perspective view of a piece of material showing a typical first set of folds;

FIG. 3(b) is a perspective view of the piece of material folded according to FIG. 3(a) and showing a second folding operation;

FIG. 3(c) is a perspective view of the piece of material folded according to FIG. 3(b) and showing a typical third folding operation;

FIG. 3(d) is a perspective view of a typical completely folded pad of material;

FIG. 4 is a top view of the rotary knife means with the knives in engagement at the cutting station for cutting the web of material into individual pieces;

FIG. 5 is an end view, partially broken, of the inner and outer rotary knife means taken along lines 5—5 of FIG. 4;

FIG. 6 is a sectional view taken along lines 6—6 of FIG. 4;

FIG. 7 is a fragmentary side view of the inner knife means taken along lines 7—7 of FIG. 6;

FIG. 8 is a fragmentary side view of the reciprocating mechanism of the inner knife means taken along lines 8—8 of FIG. 4;

FIG. 9 is a side view of the ironer station;

FIG. 10 is a top view of the ironer station taken along lines 10—10 of FIG. 9;

FIG. 11 is an end view of the ironer station taken along lines 11—11 of FIG. 9;

FIG. 12 is a side view of the stacking station;

FIG. 13 is an end view of the stacking station taken along lines 13—13 of FIG. 12;

FIG. 14 is a view similar to FIG. 12 but showing the lay-up fingers in phantom at an intermediate position and showing the pad lifting device in the operative position;

FIG. 15 is a partial sectional view of the continuous motion center guard taken along lines 15—15 of FIG. 2;

FIG. 16 is a partial view taken along lines 16—16 of FIG. 15;

FIG. 17 is a partial front view of a modified presser foot mechanism;

FIG. 18 is a sectional view taken along lines 18—18 of FIG. 17; and

FIG. 19 is a sectional view taken along lines 19—19 of FIG. 17.

DESCRIPTION OF THE PREFERRED EMBODIMENT

Figure 1:
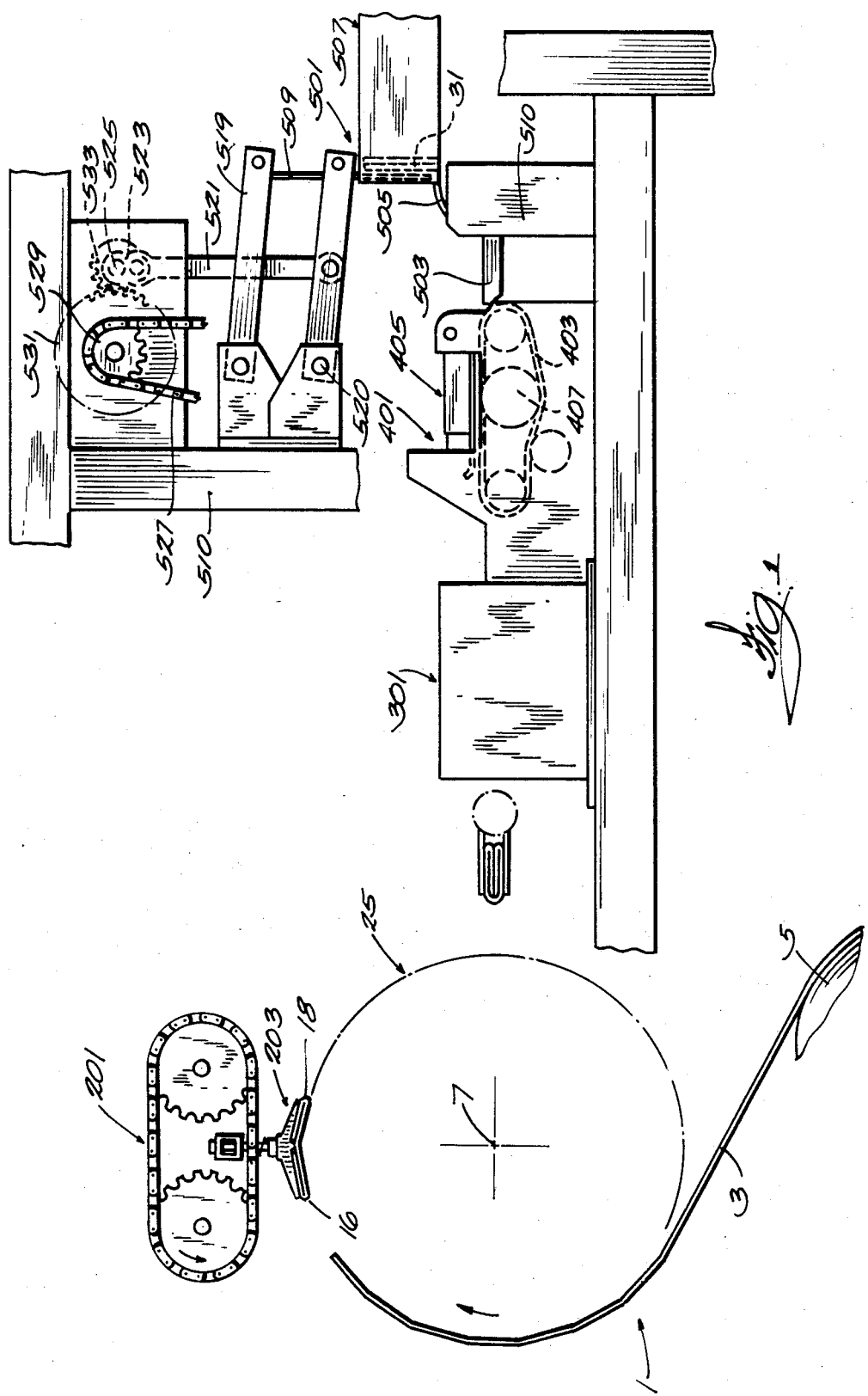
FIG. 1 is a partially schematic side view of the folded pad manufacturing system of the present invention.

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

General

FIG. 1 shows in schematic form the overall arrangement of the manufacturing system comprising the present invention. The system is particularly well adapted to manufacture folded gauze pads useful as surgical sponges. However, it will be recognized that the present invention is not limited to that application, but rather is useful in handling paper and other materials for various purposes. The system includes a rotary drum means 1, a continuous motion center guard 201, a transfer station 301, an ironing station 401, and a stacking station 501.

Flexible material may be supplied at the input end of the manufacturing system in the form of a continuous web 3 unwound from a roll of material 5. The web is unwound from the roll by clockwise rotation of drum means 1 relative to FIG. 1 about horizontal axis 7. The surface of the drum means may be coated with a substance to which the web tends to cling. Referring to FIG. 5, reference numeral 9 indicates the cutting station at which web 3 is cut into discrete pieces 11. In accordance with the present invention, the cutting operation is performed by cooperating outer knife means 13 and inner knife means 15.

While the drum means 1 rotates clockwise from the cutting station 9, notched folding paddles 17, 19 (FIG. 2) fold the piece along two longitudinal fold lines 16, 18, as shown in FIGS. 2 and 3(a). As the drum means continues to rotate so that the folded piece 11 approaches the uppermost position of the drum, presser feet 203, FIGS. 1 and 2, or presser feet 203', FIG. 19, engage the folded piece. The folding paddles unfold while the presser feet firmly hold the piece in place on the drum means. Continued rotation of the drum means carries the piece out of engagement with the presser feet. Folding paddles 21, 23 (FIG. 2) then operate to fold the piece along a third longitudinal fold line 24, as shown in FIGS. 2 and 3(b).

Reference numeral 25 (FIG. 1) represents the take-off point at which the folded piece 11 is removed from the drum means by the mechanism of transfer station 301. At the transfer station, the piece is folded along two transverse fold lines 27, 29 (FIG. 3(c)) to form a folded pad 31 as shown in FIG. 3(d).

The mechanism of the transfer station 301 transfers the pad 31 to the ironing station 401, FIG. 1. The pad is deposited on a moving belt 403 which travels in a clockwise direction with respect to FIG. 1. In keeping with the invention, the pad passes between heated shoe means 405 and a pressure roller 407 to uniformly iron the pad. The ironer station includes force means and heat-producing means to apply correct ironing force and temperature to the pad.

From the ironer station 401, the belt 403 conveys the pad 31 to a stacking station 501. The belt passes the pad onto lay-up fingers 503. The lay-up fingers pivot between the horizontal position shown in FIG. 1 and a vertical position to urge the pads along chute guides 505 to stack the pads on edge in discharge chute 507. The lay-up fingers pivot in synchronization with shutter plate 509, which prevents the stacked pad from falling backwards out of the chute. A counter circuit activates a pad displacement mechanism 511 (FIG. 13) which vertically displaces predetermined pads a suitable distance relative to the remaining pads. From the discharge chute the pads are packaged and otherwise prepared for shipment.

Drum and Cutting Means

Referring to FIGS. 2 and 5, drum means 1 rotates clockwise about axis 7. The drum and the machinery for rotating it may be of known construction and form no part of the present invention. For example, the drive machinery may include a conventional sprocket 8, FIG. 4, driven by a chain, not shown, together with suitable connectors 10 for driving drum plate 12 about axis 7 in conjunction with the sprocket. A second drum plate, not shown, is provided at the opposite end of the drum means. As the drum means rotates, it withdraws a flexible material, such as gauze, in the form of a continuous web 3 from a supply source 5. The periphery of the drum means consists of four sets 20 of notched folding paddles of known construction, FIG. 2. Each set of folding paddles consists of outer paddles 17, 19 and inner paddles 21, 23. The outer surfaces of the paddles may be coated with a substance to which the gauze tends to cling; a suitable material is sold under the trademark "Grip-Tape".

In FIGS. 2 and 5, reference numeral 9 indicates the cutting station, which may be located on a horizontal center line of the drum means. The web 3 is cut at the cutting station at a location between adjacent sets 20 of folding paddles, that is, between the trailing edge of paddle 19 of one set and the leading edge of paddle 17 of the following set.

In accordance with the present invention, the web is cut by the cooperation of outer knife means 13 and inner knife means 15. The outer knife means includes a shaft 33 which rotates in synchronization with the drum means 1 and inner knife means 15. The shaft 33 is journalled in suitable bearings 34 of conventional design mounted in the machine frame, not shown in FIG. 4. The shaft is rotated by known means in timed relationship to the speed of the drum means 1 in a counterclockwise direction with respect to FIG. 5. The actual relationship between the rotational speeds of the outer knife means and the drum means depends on the number of inner and outer knives employed, which in turn depends on the drum diameter and the number of pieces of material around the drum periphery. By way of example, in the embodiment illustrated in FIGS. 4 and 5, the outer knife means employs two cutting knives 47. Support arms 35 are firmly fixed to both ends of shaft 33 to rotate with the shaft. Pins 37, 39 are rotatably mounted in the outer ends of the arms 35. Suspended from the inner end of each pin 37 and from both ends of each pin 39 are blade supports 41, each of which comprises an angle 43 and two end extensions 45. The end extensions 45 are securely fastened to the pins 37, 39 to rotate therewith. Knives 47 are resiliently secured to the angles by means of cap screws and springs 48, FIG. 5. It will be noticed from FIG. 4 that most of the components of the outer knife means 13 are shown in duplicate. The reason is that the illustrated embodiment of the present invention incorporates apparatus for handling two identical side-by-side manufacturing lines. Since the manufacturing lines are identical, the description of only one is considered to be necessary. Of course, the invention is not limited to a dual configuration, but may include more or fewer than two lines. In fact, while the invention will be described in connection with a preferred embodiment, it will be understood that it is not intended to limit the invention to that embodiment. On the contrary, it is intended to cover all alternatives, modifications, and equivalents as may be included within the spirit and scope of the invention as defined by the appended claims.

Referring to FIG. 5, reference numeral 46 indicates the flat planar cutting surface of outer knife 47. Reference numeral 72 indicates the planar cutting surface of inner knife 73, as will be fully explained hereinafter. The cutting surfaces 46, 72 cooperate at the cutting station 9 to cut the web 3. It will be appreciated that the cutting operation does not occur instantaneously at the exact location shown in FIG. 5. Rather, the cutting operation occurs throughout several degrees of rotation of the inner and outer knife means, during which the inner and outer knives gradually engage and disengage. To enable the cutting surface 46 to properly engage cutting surface 72, it is necessary that the cutting surface of knife 47 maintain a plane that is radial with respect to axis 7 during the cutting operation. That is accomplished in the present invention by pivotting the blade support 41 about pins 37, 39, FIGS. 4 and 5. For that purpose, a pinion 50 is fixed to the outer end of each pin 37, and a gear segment 49 which meshes with the pinion is fixedly attached to each end of shaft 51. Each shaft 51 is supported for rotation in appropriate bearings within arms 35. A cam arm 53 is also fixedly attached to each end of the shaft 51 so that the cam arm 53, shaft 51, and gear segment 49 pivot in unison about the axis of shaft 51. Each cam arm is provided with a cam roller 55 which is guided in a cam track 57. The cam track is cut into a cam body 59, one of which may be fastened to each end of the stationary machine frame, not shown, by appropriate fasteners 61. As the shaft 33 rotates, cam roller 55, being guided in cam track 57, causes the cam arm 53 and gear segment 49 to pivot about shaft 51. Through the meshing of the gear segment and pinion, the blade support 41 pivots about the pins 37, 39. Thus the proper configuration of cam track 57 enables the plane of the cutting surface of knife 45 to continuously intersect axis 7 for properly engaging the inner knife means as the outer knife means rotates through the cutting station 9.

In accordance with a further aspect of the invention, the inner knife means 15 rotates about axis 7 to engage outer knife means 13 at the cutting station 9. This is accomplished in the preferred construction by providing, for example, four sets of inner knife means circumferentially spaced at 90° about axis 7. The inner knife means are located inside the four sets of notched paddles 20. Since the construction of each inner knife means is identical, only one is shown in FIGS. 4 and 5, and only one will be described. To enable each inner knife means to rotate in unison with the drum means 1, a drive bar 63 is mounted between the two drum plates 12, only one of which is shown in FIG. 4, to rotate therewith. Supports 65 for supporting rod 67 are attached to the drive bar 63 at spaced intervals. The rod 67 is fixed both axially and rotationally relative to the supports 65. Hubs 69 are suspended from the rod 67 for relative longitudinal and rotational movement thereto, as will be more fully explained. Knife plate 71 is secured to and supported by hubs 69. Inner knife 73 is firmly attached to knife support 71 by appropriate fasteners 75. Each of the four inner knives 73 protrude through the gap between two adjacent sets of folding paddles 20, as shown in FIG. 5.

In operation, the inner knife means 15 rotates in unison with the drum means 1, as previously described. In the present instance, the outer knife means 13 rotates at twice the speed and in the opposite direction as the drum means. Thus, each knife 45 cooperates with two different knives 73 to cut the web 3 at cutting station 9. To compensate for slight misalignments and manufacturing tolerances between the inner and outer knife means, adjustment means 77 are provided, FIG. 6. In the preferred embodiment, the adjustment means allows for rotation of knife 73 about the rod 67. The knife adjustment means may include a plurality of guide rollers 79, each guide roller being formed integrally with an eccentric stud portion 81. The stud portion 81 terminates in a threaded end 83, which is furnished with a nut 85 to secure the roller 79 to drive bar 63 in corresponding apertures spaced between supports 65. A lug 87 depends from each end of and is rigidly fastened to knife support 71 in the region of hubs 69, FIG. 7. The length of each lug equals the diameter of guide rollers 79. A lower plate 89 joins the two lugs and is secured to them. To rotate the knife 73 about the rod 67 for proper adjustment of the knife 73 with a knife 45, the guide rollers 79 are turned about studs 81 until the proper engagement is obtained, and the nuts 85 are then tightened.

To efficiently cut woven material such as gauze, it is highly desirable that the knives 45 and 73 translate longitudinally relative to each other during the cutting process, as indicated by arrow 92 in FIG. 8. This is accomplished in the present instance by a reciprocating means 91, as shown in FIGS. 4 and 8. The reciprocating means 91 includes a stud 93 attached to each end of each knife support 71. A bearing link 95 is pivotally mounted over each stud 93. A rod 97 connects the bearing links at the inner ends of adjacent knife supports 71. A rod 99 connects the bearing link mounted to the stud at the outer end of a knife support 71 to another bearing link 94 which is mounted over a stud 96 fastened to a lever 98. The lever 98 pivots about a headed stub shaft 101 which is supported in a bracket 103. The bracket 103 is suitably fastened to the sprocket 8 for rotation therewith. The lever 98 carries a cam follower 105 which tracks cam 107. Cam 107 is rigidly mounted to the stationary machine frame, not shown in FIGS. 4 and 8. The cam is configured so that as the inner knife means rotates in unison with the drum means 1, the lever 98 pivots about stub shaft 101 as the knife 73 rotates through the cutting station. Thus the knife 73 reciprocates a slight distance along rod 67 to aid in cutting the web in cooperation with knife 45. To keep the cam follower 105 firmly engaged with the cam 107, a collar 109 may be fastened to the end of rod 67. A compression spring 111 is interposed between the collar and a hub 69, FIG. 4. The spring 111 acts through the support 69, knife support 71, and recirpocating means 91 to assure contact between the cam follower 105 and the cam 107.

After the web 3 is cut at the cutting station 9, the piece of material 11 is folded along fold lines 16, 18, as shown in FIGS. 2 and 3(a). The folding may be accomplished by known apparatus comprising a set of folding paddles 20. Each outer paddle 17, 19 rotates 180° in opposite directions to attain parallel side-by-side relationships with inner paddles 21, 23, respectively, thus folding outer panels 22 over onto the center section 26 of piece 11. The rotation of the outer paddles is accomplished by known apparatus, such as gears 113 attached to the ends of the paddles. The gears 113 mesh with gear segments 115 which pivot about centers 117 under the influence of conventional cam followers and cams, not shown. The centers 117 are suitably attached to the drum plates 12 (FIG. 4) to rotate therewith about axis 7.

Continuous Motion Center Guard

As previously described, the surfaces of the folding paddles 17, 19, 21, 23 of the drum means 1 may be coated with a substance which causes the piece of material 11 to cling to the paddles. Thus, after being folded, the panels 22 may tend to cling to the paddles 17, 19 as the paddles return to their stretched-out positions. To hold the panels in place against the corner section 26, the present invention provides a continuous motion center guard which engages the piece between notches in the outer paddles, as will be fully described. Referring to FIGS. 1 and 2, reference numeral 201 indicates a continuous motion center guard. In the embodiment illustrated in FIGS. 1 and 2, the center guard includes a plurality of identical presser feet 203, only one of which will be described. The presser feet travel in synchronization with the drum means in an orbit which intersects the folded piece as it approaches within about 10° of the vertical center line of the drum means. The presser feet break contact with the folded piece at about 10° past the vertical center line of the drum means, at which location the outer paddles 17, 19 have sufficiently unfolded to their stretched-out configurations.

To carry the presser feet within the center guard assembly, a chain 205 in conjunction with a conventional chain drive may be employed. The chain drive may include bearings 207, sprockets 209, and adjustment means 211; see FIGS. 15 and 16. In the illustrated construction, a link 213 of chain 205 has fastened thereto an L-shaped bracket 215. A standard 217 is suitably fastened to the L-shaped bracket. The standard 217 is formed with a round aperture at its lower end to rotatably receive a pivot pin 219 which is firmly fixed to an L-shaped pivot arm 221. The lower end of the pivot arm 221 supports a cam roller 223 for following a cam track 225. The cam track 225 is cut into a cam body 227 which may be permanently attached to the stationary machine frame 229. The upper end of the pivot arm 221 bears support member 231.

To resiliently engage a folded piece of material 11, the presser feet are suspended on a plurality of support rods 235, FIGS. 1 and 2. The support rods pass through the support member 231' and are guided by upper and lower bushings 237 pressed into the support member. To provide longitudinal adjustment of the presser feet, a stop collar 239 is fixed to the upper end of each support rod. The lower ends of the support rods are threaded to receive nuts 241 and a creaser bar 233. Interposed between the bottom of support member 231' and the nuts 241 are compression springs 245. The nuts 241 and creaser bar 233 embrace a foot 247 which is shaped to fit within the notches 248 of folding paddles 17, 19, FIG. 15. Each foot is formed with a rectangular slot to receive the creaser bar, FIG. 2, to assist in creasing the piece of material 11 prior to folding it along fold line 24 (FIG. 3(b)). The lower portion of the creaser bar may be constructed as a sharp V 249, as shown in FIG. 2. The portion of the cam track 225 that corresponds to the angle of contact is not parallel to the path of the folded piece. Rather, cam track 225 is closer to the axis 7 on the vertical center line than at the initial and final contact points.

In operation, the presser feet 203 contact the folded piece of material 11 through an angle of contact of about 20° of rotation of the drum means 1. For that purpose, the orbit of the presser feet intersects the path of the folded piece on the drum periphery when the center of the piece is within about 10° of the vertical center line of the drum means. At that point, the cam roller 223, under the guidance of cam track 225, orients the presser feet such that support rods 235 are directed toward axis 7. The cam track is configured so that it rotates the cam roller and presser feet clockwise relative to FIG. 2 about pivot pin 219 (FIG. 16) as the presser feet are carried by the chain 205 at the same speed as the piece of material. Under the influence of the cam track, support rods 235 are always directed toward axis 7 throughout the angle of contact between the presser foot and the drum means. The last point of contact is about 10° past the vertical center line of the drum means. At that point, the outer folding paddles 17, 19 have sufficiently disengaged from the folded panels 22. Because of the non-parallel paths of the presser foot and the periphery of the drum means through the angle of contact, the feet 247 and the creaser bar 233 are pushed upward by the folded piece and drum means against springs 245. The the V 249 of the creaser bar creases the piece along fold line 24 (FIG. 3(b)) for ease of subsequent folding.

After leaving the final point of contact with the presser feet 203, the piece 11 is folded along fold line 24, FIG. 3(b). That is accomplished by rotating inner folding paddles 21, 23 approximately 90° toward each other so that the paddles attain a parallel side-by-side relationship, FIGS. 1 and 2. The rotation is accomplished through conventional gears 251 attached to the inner folding paddles, FIG. 2. The gears 251 are actuated by known gear segments actuated through conventional cam and cam followers, not shown.

Transfer Station

When the folded piece of material 11 reaches the take-off point 25 of the drum means 1, the inner paddles 21, 23 open, and the piece is removed from the drum by the mechanism of the transfer station 301. In addition, the mechanism of the transfer station folds the piece along two additional fold lines 27, 29, as shown in FIG. 3(c). It will be noticed that fold lines 27, 29 are perpendicular to fold lines 16, 18, and 24. Thus, when the piece emerges from the transfer station, it is completely folded into a finished pad 31, as shown in FIG. 3(d).

Ironing Station

Further in accordance with the present invention, the folded pad 31 is ironed at an ironing station 401. Referring to FIGS. 1 and 9, the mechanism of the transfer station 301 deposits the pad 31 onto a belt 403. The belt travels in a clockwise direction with respect to FIGS. 1 and 9, as illustrated by arrow 404. The belt is driven by crowned rollers 409 under the action of conventional belt and pulley means 411.

To uniformly iron the pads 31, the present invention provides an ironing zone 414 located between a heated shoe 405 and a pressure roller 407. The heated shoe 405 includes a heater block 415 and an ironer plate 417. To provide heat for the pad 31, the heater block may be formed with suitable apertures 419 for receiving conventional electric heating elements, not shown. The heating elements may be connected in any convenient manner to a source of electrical power. The ironer plate 417, which has a smooth lower ironing surface 421, is joined to the bottom of the heater block by any suitable means and conducts heat from the heater block to the ironing surface 421.

The belt 403, which is preferably composed of a material to which gauze tends to cling, conveys the pad toward the inlet 423 of the ironing zone 414. To allow the pad to enter the ironing zone, the heated shoe 405 is capable of opening and closing. This is accomplished in the present instance by furnishing the exit end 424 of heater block 415 with a pair of lugs 425. The lugs 425 are adapted to receive and rotate about pins 427 firmly fixed in machine frame 429. The lugs are fastened to the heater block by suitable fasteners, but an insulating strip 431 is sandwiched between the lugs and the heater block. An L-shaped extension arm 433 is fastened to the inlet end of the heater block, and an insulating strip 435 separates the extension arm from the heater block. The extension arm extends laterally of the heated shoe and carries a cam follower 437, as shown in FIGS. 10 and 11. Cam follower 437 is actuated by cam 439, which rotates in unison with drive shaft 441. Thus, the shoe 405 pivots about pins 427 under the influence of the cam 439 to open at the inlet 423. To enhance the ability of the pad to enter the ironing zone 414, the ironer plate 417 may be curved upward in sled-runner fashion at the inlet end, FIG. 9.

To close the shoe 405 after the pad 31 has entered the ironing zone 414 and to apply the correct ironing force to the pad, the ironing station of the present invention includes force means 442. The force means preferably comprises spring-loaded plungers 443, the upper ends of which are guided in horizontal bar 445 of frame 429. The plungers may be threaded to accommodate nuts 447, 449. The horizontal bar 445 and a compression spring 450 are interposed between the nuts 447, 449. The lower end of each plunger rests on a button 451, which is rotatably mounted on a shoulder screw 453. Each shoulder screw 453 screws into a tab 455 attached to the inlet side of extension arm 433. The spring-loaded plungers allow the cam 439 to open the shoe, and the plungers close the shoe in timed relationship to a pad 31 entering the ironing zone 414. In the closed position, the springs exert approximately 15 lbs. of force on the pad. The preferred ironing temperature is about 300° F. To insure that the ironed pad will detach from the belt 403 at the exit end 424 of the ironing station, an air blast device of well-known construction, not shown, may be employed.

Stacking Station

The manufacturing system includes a stacking station 501, as shown in FIG. 1 and FIGS. 12–14. Referring to FIG. 12, reference numeral 403 indicates the belt of ironing station 401. The belt conveys a folded pad 31 from the ironing station exit end 424 to the stacking station. The stacking station includes a plurality of lay-up fingers 503 fastened to a supporting angle 504. The supporting angle is suspended from a rotatable shaft 506 by means of arms 508. The shaft is supported in machine frame 510 by appropriate bearings, not shown.

To facilitate packaging or otherwise handling the ironed pads 31, the stacking station 501 incorporates a discharge chute 507. The chute may be mounted to the frame 510 by any suitable means, as for example, welding in conjunction with brace 513. The chute includes a floor 515 which extends beyond side walls 517 in the form of a plurality of spaced chute guides 505.

In operation, the ironer belt 403 deposits a pad 31 onto the top surface of lay-up fingers 503. The fingers then rotate 90° clockwise with respect to FIG. 12 to convey the pad along chute guides 505 to stack the pad on an edge within the chute 507.

Referring to FIGS. 1 and 12, reference numeral 509 indicates a shutter plate which reciprocates in a vertical plane within the chute 507. To prevent stacked pads 31 from falling backward out of the chute, the shutter plate reciprocates in synchronization with the lay-up fingers 503 to rise out of the chute as the fingers push a pad into the chute and the shutter plate descends into the chute behind the last pad as the fingers return to the horizontal position to pick up a new pad. The shutter plate is actuated through a double-bar linkage 519 and drive arm 521. The double-bar linkage pivots about studs 520 fixed to machine frame 510. The lower end of the dirve arm may be rotatably attached to the lower bar of the doublebar linkage. The upper end of the drive arm may be rotatably attached to an eccentric 523, which is attached to and rotates with shaft 525. Shaft 525 is driven by conventional drive means which may consist of a chain 527 and sprocket 529 and a pair of meshing gears 531, 533, FIG. 1.

The stacking station includes a pad displacement means 511 to vertically displace predetermined pads 31' within chute 507 relative to the other pads 31, FIG. 14. The vertical displacement means comprises a plurality of lifting fingers 535, each of which is supported by a block 537. The lifting fingers lie within the spaces between the chute guides, FIG. 13. The blocks 537 are fixed relative to rotatable shaft 539. Also fixed to shaft 539 is one end of a lever 541. The second end of lever 541 is pivotally attached, as by a shoulder screw 544, to an actuating means. The activating means includes an electric solenoid 543, and the lever 541 is connected to the solenoid plunger 545.

In normal operation, the lifting fingers 535 lie in the same plane as chute guides 505, as shown in FIG. 12. In this situation, the pads 31 slide up the chute guides 505 and lifting fingers 535 under the influence of fingers 503 and come to rest on the floor 515 of chute 507. Well-known electronic controls, not shown, count the number of pads entering the chute. To provide visual indications of the number of pads entering the chute, the controls are programmed to actuate the solenoid 543 after a predetermined number of pads has entered the chute. Actuation of the solenoid causes plunger 542 to retract, that is, to move upward with respect to FIG. 13. This causes lever 541, blocks 537, and lifting fingers 535 to rotate counterclockwise relative to FIG. 12 and to attain the position shown in FIG. 14. In that situation, the pad 31' pushed up the lifting fingers 535 enters the chute at a higher elevation than the remaining pads 31. The shutter plate 509 opens to allow the pad 31' to enter the chute and then closes behind the pad 31' to hold it pressed in place against the other pads 31 in the raised position. Thus, a convenient visual means is provided for dividing the stacked pads into complements of any desired number for packaging or other processing.

It will be understood that all of the components of the manufacturing system of the present invention operate simultaneously. Furthermore, the apparatus at each station cooperates in timed relationship with the preceding and following stations to continuously manufacture folded pads from a supply roll of material.

FIGS. 17 to 19 depict a modified continuous motion center guard 201'. The center guard 201' includes a plurality of identical presser feet 203' which travel in synchronization with the drum means 1 in orbits which intersect the drum periphery. As shown in FIG. 19, the presser feet contact the folded piece 11 as it approaches within about 10° of the vertical center line of the drum means and breaks contact with the folded piece at about 10° past the vertical center line. This is accomplished in the construction illustrated in FIGS. 17 to 19 by revolving the presser feet in ferris wheel fashion about horizontal axis 253 in the direction of arrow 254, FIG. 18.

Axis 253 corresponds to the longitudinal axis of a center shaft 255 which is mounted at its opposite ends for oscillation within conventional bearings 257, FIG. 17. The bearings 257 are fastened to a stationary frame member 259. Only one bearing 257 and frame member 259 are shown in FIG. 17, but it will be understood that both bearings and frame members are substantially similar. Fixedly attached near opposite ends of the shaft 255 are a pair of sun gears 260; only one gear is shown in FIG. 17. The gears 260 may be attached to the shaft by any well known means, such as by a fastener through a gear hub 262. The shaft 255 and gears 260 do not rotate about axis 253, but rather they oscillate periodically about axis 253 under the direction of linkage 264. In the structure illustrated in FIGS. 17 and 18, the linkage 264 includes a crank 266 secured to the shaft, a link 268 pivotally connected to the crank as by pin 270, and an elongated rod 272. The rod 272 is preferably axially adjustable with respect to the link 268. The distal end of rod 272 is in operative relation to a conventional driving member, not illustrated in FIGS. 17 and 18, which causes the rod to reciprocate along its longitudinal axis, thereby causing the crank 266, shaft 255, and gears 260 to oscillate for a purpose to be fully described hereinafter.

To revolve the presser feet 203' about axis 253, a pair of axially spaced drivers 261 are mounted for rotation relative to the shaft 255 by means of conventional bearings, not shown. Only one driver 261 is shown in FIG. 17. The drivers are rotatably driven about shaft 255 by a pair of chains 263 which engage sprockets 265. The sprockets 265 may form an integral part of the drivers. Each driver further includes an arm 267. The arms of the two drivers are angularly aligned. Each arm is adapted to carry at least one and preferably two idler gears 269 which rotate freely within the arm. The idler gears 269 of each arm mesh with a corresponding sun gear 260. Each arm further carries preferably two driven gears 271 which are also free to rotate within the arm. Each driven gear 271 meshes with a corresponding idler gear 269. The driven gears and the sun gears have equal numbers of teeth.

Suspended between two spaced and longitudinally aligned gears 271 is a support member 231'. Each support member is provided with a generally L-shaped bracket 273 joined to the underside at both ends. The brackets 273 are connected through a conventional adjustment device 275 to a projection 277 extending from the driven gears. By means of adjustment device 275, the ends of the support members may be independently positioned with respect to axis 253 and drum means axis 7.

As previously described in connection with the operation of the continuous motion center guard depicted in FIGS. 1 and 2, the presser feet 203' resiliently engage a folded piece of material 11. This is accomplished by suspending the presser feet on support rods 235'. The support rods pass through the support member 231' and are guided by upper and lower bushings 237' pressed into the support member. To provide longitudinal adjustment of the presser feet, a stop collar 239' is fixed to the upper end of each support rod. The lower ends of the support rods are threaded to receive nuts 241' and a creaser bar 233'. Interposed between the bottom of support member 231' and the nuts 241' are compression springs 245'. The nuts 241' and creaser bar 233' embrace a foot 247' which is shaped to fit within the notches 248 of folding paddles 17 and 19, FIG. 15. Each foot is formed with a rectangular slot 278 to receive the creaser bar, FIG. 19. The creaser bar assists in creasing the piece of material 11 prior to it being folded along fold line 24, FIG. 3 (b). The lower portion of the creaser bar may be constructed as a sharp V 249', as shown in FIG. 19.

In operation, the drivers 261 are rotated by chains 263 so that the orbital speed of the presser feet 203' is the same as the peripheral speed of the drum means 1. For that purpose, chains 263 may be driven by any suitable device, such as a timed drive shaft, not shown, in synchronization with the rotation of the drum means. As the drivers rotate in the direction of arrow 254, they cause idler gears 269 to revolve about axis 253. In addition, due to their being in mesh with the generally fixed sun gears 260, the idler gears also rotate about their longitudinal axes. In a similar manner, driven gears 271 also revolve about axis 253. However, because the number of teeth on the sun gears and driven gears are equal, the driven gears do not rotate about their longitudinal axes. Instead, the driven gears maintain their initial rotational attitude as they revolve about axis 253. Thus, the presser feet 203' maintain their generally vertical attitude with respect to FIGS. 18 and 19 as they revolve about axis 253.

As the presser feet 203' approach the periphery of drum means 1 to intersect it in the region 279 (FIG. 19), the rod 272 is positioned such that it is at the extreme right of its reciprocating path. As a result, the presser feet are oriented as illustrated at 281 when they contact the folded piece of material 11. This occurs when the piece of material is about 10° before the drum means vertical center line. As the presser feet and drum means travel together toward the drum means vertical center line, the feet 247' and creaser bar 233' are forced upwardly by the folded piece and drum means against springs 245'. Consequently, the V 249' of the creaser bar creases the piece along fold line 24 (FIG. 3(b)) for ease of subsequent folding.

Simultaneously with the mutual rotation of the drum means 1 and the presser feet 203', the rod 272 continuously reciprocates toward the left as seen in FIGS. 18 and 19. As a result, the sun gears 260 oscillate clockwise, and they cause driven gears 271 to also oscillate clockwise through the idler gears 269. The oscillation of the driven gears 271 causes oscillation of the support member 231' suspended between them. The timed relationship between the rotation of the drum means, the orbiting of the support member about axis 253, and the oscillation of the support member about the longitudinal axes of driven gears 271 is such that the longitudinal axes of the support rods 235' are variably oriented to pass through the drum means axis 7 throughout the period of mutual contact between the piece of material 11 and the presser feet. When the folded piece is about 10° past the drum means vertical center line, the presser feet acquire the orientation indicated by reference numeral 283, FIG. 19. The springs 245' are then relieved of their creasing force, and the presser feet break contact with the folded piece of material. At the final orientation 283, the rod 272 is at the extreme left of its reciprocating path. The rod then undergoes reciprocation to the right to oscillate the presser feet to the proper orientation 281 for the next cycle of contact with a folded piece of material.

Thus, it is apparent that there has been provided, in accordance with the invention, a fully integrated assembly of apparatus for manufacturing folded pads that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall with the spirit and broad scope of the appended claims.

We claim:

1. An improved apparatus for cutting a continuous web of flexible material withdrawn from a supply source by a drum means mounted in a machine frame for rotation about a drum axis and having a cutting station thereon, and for folding the cut piece of material, wherein the improvement comprises:
   a. a rotary inner knife means mounted to the drum means for rotation in unison with the drum means, the rotary inner knife means including at least four inner cutting knives;
   b. a rotary outer knife means journalled in the machine frame and rotated in timed relationship with the drum means about a second axis parallel to the drum axis for cooperatively engaging the inner knife means at the cutting station to cut the web, the rotary outer knife means including at least two outer cutting knives that cooperate with alternate inner cutting knives to cut the web at the cutting station, and wherein each outer cutting knife is resiliently fastened within the rotary outer knife means, and wherein each outer cutting knife is formed with a generally planar cutting surface that substantially intersects the drum axis throughout several degrees of rotation as the outer cutting knife rotates through the cutting station;
   c. folding means mounted to the drum means for folding the flexible material cut at the cutting station; and
   d. guard means mounted to the machine frame above the drum means for holding a cut and folded piece of flexible material on the periphery of said drum means during a predetermined portion of each revolution of the drum means.

2. An improved apparatus for cutting a continuous web of flexible material withdrawn from a supply source by a drum means mounted in a machine frame for rotation about a drum axis and having a cutting station thereon, and for folding the cut piece of material, wherein the improvement comprises:
   a. a rotary inner knife means mounted to the drum means for rotation in unison with the drum means;
   b. a rotary outer knife means journalled in the machine frame and rotated in timed relationship with the drum means about a second axis parallel to the drum axis for cooperatively engaging the inner knife means at the cutting station to cut the web, wherein the rotary outer knife means comprises:
      i. rotary support means journalled in the machine frame for rotation about the second axis;
      ii. at least one blade support means suspended for pivoting within the rotary support means about a third axis parallel to the drum axis; and
      iii. actuating means mounted to the rotary support means and guided by the machine frame to pivot the blade support means about the third axis with respect to the rotary support means;

c. folding means mounted to the drum means for folding the flexible material cut at the cutting station; and d. guard means mounted to the machine frame above the drum means for holding a cut and folded piece of flexible material on the periphery of said drum means during a predetermined portion of each revolution of the drum means, so that rotation of the rotary support means within the machine frame actuates the blade support means for pivoting with respect to the rotary support means.

3. The improved cutting apparatus of claim 2 wherein the blade support means includes a cutting knife having a generally planar cutting surface, and wherein the blade support means pivots with respect to the rotary support means about the third axis to orient the plane of the knife cutting surface to continuously intersect the drum axis throughout several degrees of rotation while the cutting knife rotates through the cutting station.

4. An improved apparatus for cutting a continuous web of flexible material withdrawn from a supply source by a drum means mounted in a machine frame for rotation about a drum axis and having a cutting station thereon, and for folding the cut piece of material, wherein the improvement comprises:

a. a rotary inner knife means mounted to the drum means for rotation in unison with the drum means;

b. a rotary outer knife means journalled in the machine frame and rotated in timed relationship with the drum means about a second axis parallel to the drum axis for cooperatively engaging the inner knife means at the cutting station to cut the web, wherein the rotary outer knife means comprises:

i. a central shaft journalled in the machine frame, the central shaft having at least one pair of support members fastened at spaced intervals thereto;

ii. at least one pair of coaxial pins pivotably mounted within the support members;

iii. a blade support suspended between the pins for pivoting therewith;

iv. a cutting knife resiliently attached to each blade support, the knife having a generally planar cutting surface;

v. cam follower means journalled in the support members;

vi. engagement means mounted to the cam follower means for pivoting the blade support in response to actuation of the cam follower means; and vii. cam means mounted to the machine frame for actuating the cam follower means;

c. folding means mounted to the drum means for folding the flexible material cut at the cutting station; and d. guard means mounted to the machine frame above the drum means for holding a cut and folded piece of flexible material on the periphery of said drum means during a predetermined portion of each revolution of the drum means, so that rotating the central shaft actuates the cam follower means for pivoting the cutting knife about the pins to orient the plane of the knife cutting surface to continuously intersect the drum axis through several degrees of rotation as the cutting knife rotates through the cutting station.

5. An improved cutting apparatus for cutting a continuous web of flexible material withdrawn from a supply source by a drum means rotatably mounted in a machine frame for rotation about a drum axis and having a cutting station thereon, and for folding the cut piece of material, wherein the improvement comprises:

a. a rotary inner knife means mounted to the drum means for rotation in unison with the drum means comprising at least one support means fastened to the drum means for rotation in unison therewith, a knife support mounted to each support means, and an inner cutting knife attached to the knife support, the knife protruding beyond the periphery of the drum means, the inner cutting knife being formed with a generally planar cutting surface, the plane of the knife cutting surface substantially intersecting the axis of the drum means, the rotary inner knife means further comprising the improvement of adjusting means for radially adjusting the inner cutting knife relative to the drum means, wherein the adjusting means comprises:

i. a rod rigidly mounted to the support means for pivotally mounting the knife support, the knife support being formed with at least one pocket; and ii. at least one stud adjustably mounted in the support means, the stud terminating in a non-coaxial cylindrical roller fitting snugly within the pocket in the knife support;

b. a rotary outer knife means journalled in the machine frame and rotated in timed relationship with the drum means about a second axis parallel to the drum axis for cooperatively engaging the inner knife means at the cutting station to cut the web; and c. guard means mounted to the machine frame above the drum means for holding a cut and folded piece of flexible material on the periphery of the drum means during a predetermined portion of each revolution of the drum means.

6. An improved cutting apparatus for cutting a continuous web of flexible material withdrawn from a supply source by a drum means rotatably mounted in a machine frame for rotation about a drum axis and having a cutting station thereon, and for folding the cut piece of material, wherein the improvement comprises:

a. a rotary inner knife means mounted to the drum means for rotation in unison with the drum means comprising at least one support means fastened to the drum means for rotation in unison therewith, a knife support mounted to each support means, and an inner cutting knife attached to the knife support, the knife protruding beyond the periphery of the drum means, the inner cutting knife being formed with a generally planar cutting surface, the plane of the knife cutting surface substantially intersecting the axis of the drum means, and wherein the inner knife means further comprises the improvement of reciprocating means for longitudinally reciprocating the knife support relative to the rotary outer knife means while the inner and outer cutting knives are cooperating to cut the web at the cutting station;

b. a rotary outer knife means journalled in the machine frame and rotated in timed relationship with the drum means about a second axis parallel to the drum axis for cooperatively engaging the inner knife means at the cutting station to cut the web; and c. guard means mounted to the machine frame above the drum means for holding a cut and folded piece of flexible material on the periphery of the drum means during a predetermined portion of each revolution of the drum means.

7. The improved cutting apparatus of claim 6 wherein the reciprocating means comprises:
   a. cam means fixed to the machine frame;
   b. cam follower means pivotally mounted to the drum means for rotation therewith in engagement with the cam means;
   c. connecting means between the knife support and the cam follower means; and
   d. spring means interposed between the support means and the knife support to urge the cam follower means into engagement with the cam means,
   so that rotating the drum means within the machine frame actuates the cam follower means to reciprocate the knife support longitudinally while the inner and outer cutting knives are cooperating to cut the web at the cutting station.

8. An improved cutting apparatus for cutting a continuous web of flexible material withdrawn from a supply source by a drum means rotatably mounted in a machine frame for rotation about a drum axis and having a cutting station thereon, and for folding the cut piece of material, wherein the improvement comprises:
   a. a rotary knife means mounted to the drum means for rotation in unison with the drum means, wherein the inner knife means comprises:
      i. at least one support means joined to the drum means for rotation therewith;
      ii. a knife support pivotally mounted to the support means and being formed with at least one pocket;
      iii. an inner cutting knife fastened to the knife support, the knife protruding beyond the periphery of the drum means;
      iv. at least one adustable stud means mounted in the support means for engaging the pocket in the knife support to adjust the knife support angularly with respect to the drum means;
      v. cam means mounted to the machine frame;
      vi. cam follower means mounted to the drum means for rotation therewith, the cam follower means being actuated by the cam means for longitudinally reciprocating the knife support relative to the rotary outer knife means while the rotary inner and outer knife means are cooperating to cut the web at the cutting station;
      vii. resilient means interposed between the support means and the knife support for urging the cam follower means into engagement with the cam means;
   b. a rotary outer knife means journalled in the machine frame and rotated in timed relationship with the drum means about a second axis parallel to the drum axis for cooperatively engaging the inner knife means at the cutting station to cut the web; and
   c. guard means mounted to the machine frame above the drum means for holding a cut and folded piece of flexible material on the periphery of the drum means during a predetermined portion of each revolution of the drum means.

9. An improved apparatus for cutting a continuous web of flexible material withdrawn from a supply source by a drum means rotatably mounted in a machine frame for rotation about a drum axis and having a cutting station thereon, and for folding the cut piece of material, wherein the improvement comprises:
   a. a rotary inner knife means mounted to the drum means for rotation in unison with the drum means;
   b. a rotary outer knife means journalled in the machine frame and rotated in timed relationship with the drum means about a second axis parallel to the drum axis for cooperatively engaging the inner knife means at the cutting station to cut the web; and
   c. guard means mounted to the machine frame above the drum means for holding a cut and folded piece of flexible material on the periphery of the drum means during a predetermined portion of each revolution of the drum means, wherein the guard means for holding the folded piece of cut material on the periphery of the drum means during a predetermined portion of each revolution of the drum means comprises continuous motion drive means mounted to the machine frame for supporting and driving the center guard means in an orbit to intersect the periphery of the drum means, wherein the continuous motion of the drive means includes at least one pair of spaced substantially similar chains arranged to travel in sychronization with the drum means in parallel planes that are perpendicular to the axis of the drum means.

10. The improved center guard apparatus of claim 9 wherein the guard means comprises:
    a. standard means joined to corresponding links of each chain for continuous orbital motion therewith;
    b. support means pivotally suspended between the standard means for pivotal motion relative thereto;
    c. at least one support rod means disposed in the support means for resilient axial movement relative thereto; and
    d. presser foot means attached to the support rod means for intersecting the periphery of the drum means,
    so that the presser foot means yields longitudinally relative to the support means to resiliently hold the folded piece of material on the drum means during a predetermined portion of each revolution thereof.

11. The improved center guard apparatus of claim 10 wherein the support means includes a cam follower fastened thereto, and wherein the machine frame includes cam means for guiding the cam follower to pivot the support means between the standard means for directing the axis of the support rod means to intersect the axis of the drum means throughout the angle of contact.

12. The improved center guard apparatus of claim 19 wherein the cam means includes a generally oval cam track disposed substantially perpendicular to the axis of the drum means, the oval track being formed with a concave portion for guiding the cam follower when the presser foot is in operative relation to the drum means throughout the angle of contact.

13. An improved apparatus for cutting a web of flexible material withdrawn from a supply source by a drum means rotatably mounted in a machine frame for rotation about a drum axis and having a cutting station thereon, and for folding the cut piece of material, wherein the improvement comprises:

a. a rotary inner knife means mounted to the drum means for rotation in unison with the drum means;

b. a rotary outer knife means journalled in the machine frame and rotated in timed relationship with the drum means about a second axis parallel to the drum axis for cooperatively engaging the inner knife means at the cutting station to cut the web; and c. guard means mounted to the machine frame above the drum means for holding a cut and folded piece of flexible material on the periphery of the drum means during a predetermined portion of each revolution of the drum means, wherein the guard means for holding the folded piece of cut material on the periphery of the drum means during a predetermined portion of each revolution of the drum means comprises continuous motion drive means mounted to the machine frame for supporting and driving the center guard means in an orbit to intersect the periphery of the drum means, and wherein the continuous motion of the drive means comprises:

a shaft mounted in the machine frame and having an axis substantially parallel to the rotational axis of the drum means;

i. at least one sun gear fixedly attached to the shaft;

ii. a pair of spaced angularly aligned driver means mounted on the shaft for rotation relative thereto;

iii. means for rotating the driver means in timed relationship to the drum means;

iv. at least one idler gear mounted for rotation in each driver means and meshing with the sun gear; and v. at least one driven gear mounted for rotation in each driver means and meshing with an idler gear, the driven gear being longitudinally aligned and adapted to rotatably support a guard means therebetween and having the same number of teeth as the sun gear, so that rotating the driver means in timed relationship to the drum means causes the guard means to contact the folded piece of material during a predetermined portion of each revolution of the drum means.

14. The improved center guard apparatus of claim 13 wherein the shaft is mounted for oscillation in the machine frame, and further comprising linkage means for oscillating the shaft and sun gear, so that actuating the linkage means in timed relationship to the rotation of the drum means and driver means causes the guard means to contact the folded piece of material at continuously variable and predetermined orientations with respect to the drum means during a predetermined portion of each revolution of the drum means.

15. The improved center guard apparatus of claim 14 wherein the guard means comprises:

a. at least one support member;

b. bracket means attached to each longitudinally aligned driven gear for supporting opposite ends of the support member;

c. at least one support rod means disposed in the support member for resilient axial movement relative thereto; and d. presser foot means attached to the support rod means for intersecting the periphery of the drum means, so that the presser foot means yields longitudinally along the support rod means relative to the support member to resiliently hold folded piece of material on the drum means during a predetermined portion of each revolution thereof.

16. The improved center guard apparatus of claim 15 wherein the bracket means includes an adjustment device for adjusting the support member in a direction perpendicular to the drum means axis of rotation.

17. The improved center guard apparatus of claim 10 or claim 16 wherein the presser foot means includes at least one creaser bar for creasing the folded piece of material along a predetermined fold line.

18. The improved center guard apparatus of claim 17, wherein the presser foot means intersects the drum means to hold the folded piece of material on the periphery thereof through an angle of contact of about 20° of each revolution of the drum means.

* * * * *

UNITED STATES PATENT AND TRADEMARK OFFICE
CERTIFICATE OF CORRECTION

PATENT NO. : 4,655,739
DATED : April 7, 1987
INVENTOR(S) : Robert H. Pratt et al.

It is certified that error appears in the above—identified patent and that said Letters Patent is hereby corrected as shown below:

Column 18, Line 56    Delete "claim 19" and substitute therefor ----claim 11----

Column 19, Line 38    Before "being" delete "gear" and substitute therefor ----gears----

Signed and Sealed this

Tenth Day of November, 1987

Attest:

DONALD J. QUIGG

Attesting Officer

Commissioner of Patents and Trademarks